United States Patent [19]
Haissaguerre et al.

[11] Patent Number: 6,064,902
[45] Date of Patent: May 16, 2000

[54] PULMONARY VEIN ABLATION CATHETER

[75] Inventors: Michel Haissaguerre, Talence, France; Donald F. Patterson, North Chelmsford; James M. Fialkowski, Tewksbury, both of Mass.

[73] Assignee: C.R. Bard, Inc., Murray Hill, N.J.

[21] Appl. No.: 09/061,421

[22] Filed: Apr. 16, 1998

[51] Int. Cl.$^7$ .......................... A61B 5/0408; A61B 17/39; A61N 1/05

[52] U.S. Cl. ............................ 600/381; 600/393; 606/41; 607/99; 607/122

[58] Field of Search .................................... 600/374, 381, 600/393; 606/41; 607/99, 122

[56] References Cited

U.S. PATENT DOCUMENTS

| | | |
|---|---|---|
| 3,485,234 | 12/1969 | Stevens . |
| 3,769,984 | 11/1973 | Muench . |
| 3,924,632 | 12/1975 | Cook . |
| 3,949,757 | 4/1976 | Sabel . |
| 4,172,451 | 10/1979 | Kline . |
| 4,365,639 | 12/1982 | Goldreyer . |
| 4,402,328 | 9/1983 | Doring . |
| 4,444,195 | 4/1984 | Gold . |
| 4,522,212 | 6/1985 | Gelinas et al. . |
| 4,586,923 | 5/1986 | Gould et al. . |
| 4,592,373 | 6/1986 | Beranek . |
| 4,608,986 | 9/1986 | Beranek et al. . |
| 4,682,603 | 7/1987 | Franz . |
| 4,699,147 | 10/1987 | Chilson et al. . |
| 4,777,955 | 10/1988 | Brayton et al. . |
| 5,228,441 | 7/1993 | Lundquist . |
| 5,275,162 | 1/1994 | Edwards et al. . |
| 5,315,996 | 5/1994 | Lundquist . |
| 5,318,525 | 6/1994 | West et al. . |
| 5,322,064 | 6/1994 | Lundquist . |
| 5,364,352 | 11/1994 | Cimino et al. . |
| 5,383,852 | 1/1995 | Stevens-Wright . |
| 5,383,917 | 1/1995 | Desai et al. . |
| 5,462,527 | 10/1995 | Stevens-Wright et al. . |
| 5,545,200 | 8/1996 | West et al. . |
| 5,611,777 | 3/1997 | Bowden et al. . |
| 5,628,778 | 5/1997 | Kruse et al. . |
| 5,642,736 | 7/1997 | Avitall ....................... 606/41 |
| 5,662,606 | 9/1997 | Cimino et al. . |
| 5,782,828 | 7/1998 | Chen et al. ............... 606/41 |
| 5,885,278 | 3/1999 | Fleischman ............... 606/41 |
| 5,895,355 | 4/1999 | Schaer ....................... 606/41 |

Primary Examiner—Lee Cohen
Attorney, Agent, or Firm—Darby & Darby

[57] ABSTRACT

A catheter for ablating and/or mapping tissue on the inner wall of a blood vessel, including a body portion and a tip portion having a proximal section and a distal section, the proximal section including a proximal ablation electrode and a proximal mapping electrode and the distal section including a distal ablation electrode and a distal mapping electrode, wherein the tip portion is deflectable from a first, generally straight, configuration in which the proximal and distal sections are substantially co-linear to a second, J-shaped, configuration in which the proximal and distal sections are generally parallel with a separation therebetween substantially corresponding to the inside diameter of the blood vessel.

8 Claims, 4 Drawing Sheets

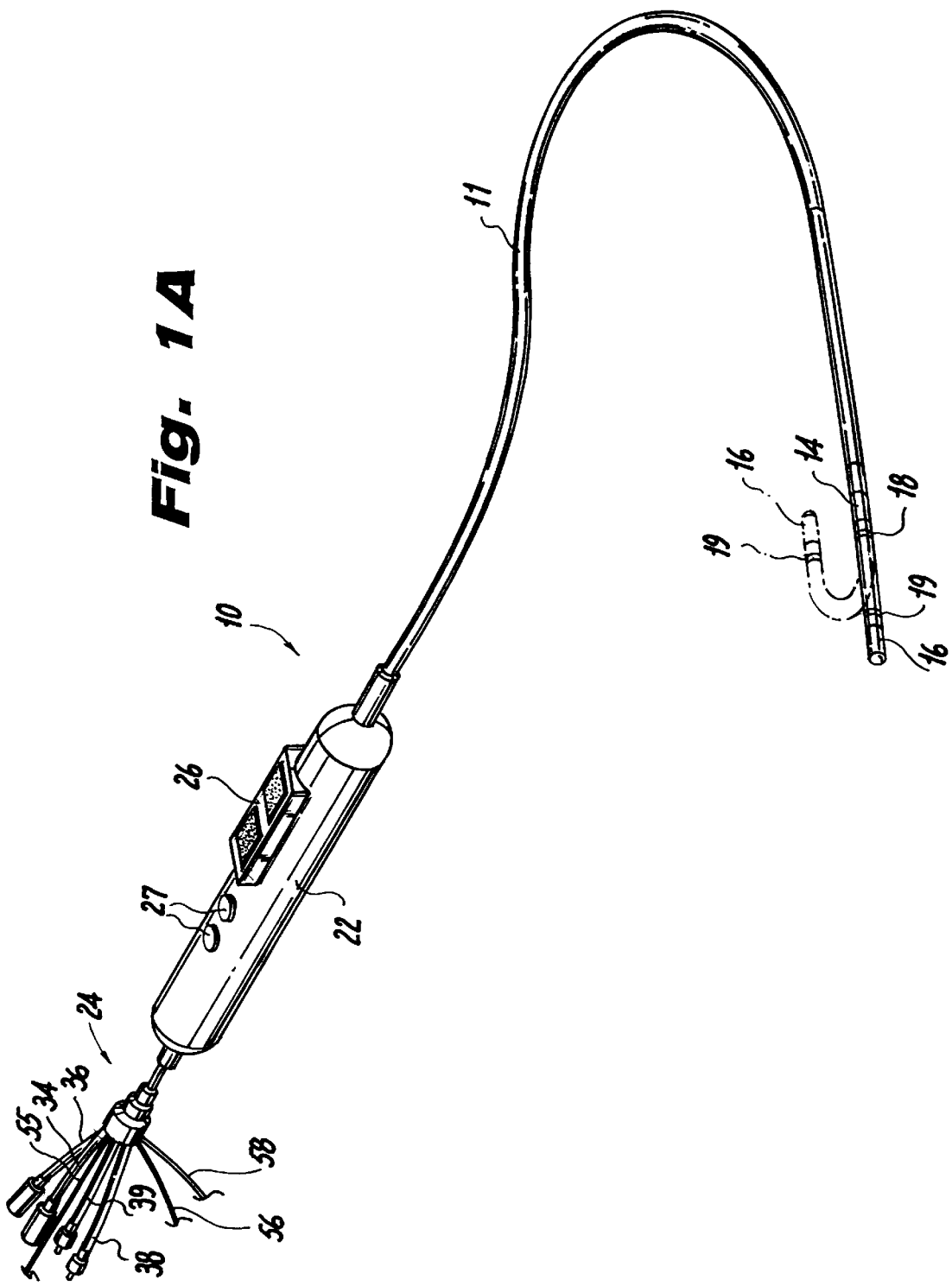

PULMONARY VEIN ABLATION CATHETER

FIELD OF THE INVENTION

The present invention relates to a steerable medical catheter and, more particularly, to a flexible, electrode-bearing catheter of the type used in electrophysiological studies for intracardiac electrocardiographic recording, mapping, stimulation and ablation.

BACKGROUND OF THE INVENTION

Catheters are often used in medical procedures to provide physical access to remote locations within a patient via a relatively small passageway, reducing the need for traditional invasive surgery. The catheter tube can be inserted into an artery or other passageway through a relatively small incision in the patient's body, and threaded through the patient's system of blood vessels to reach the desired target.

Various types of catheters are used in various procedures, both diagnostic and therapeutic. One general type of catheter used for both diagnostic and therapeutic applications is a cardiac electrode catheter. The diagnostic uses for a cardiac electrode catheter include recording and mapping of the electrical signals generated in the course of normal (or abnormal) heart function. Therapeutic applications include pacing, or generating and placing the appropriate electrical signals to stimulate the patient's heart to beat in a specified manner, and ablation. In an ablation procedure, electrical or radio-frequency energy is applied through an electrode catheter to form lesions in a desired portion of the patient's heart, for example the right atrium. When properly made, such lesions will alter the conductive characteristics of portions of the patient's heart, thereby controlling the symptoms of supra-ventricular tachycardia, ventricular tachycardia, atrial flutter, atrial fibrillation, and other arrhythmias.

Such a catheter is typically placed within a desired portion of the patient's heart or arterial system by making a small incision in the patient's body at a location where a suitable artery is relatively close to the patient's skin. The catheter is inserted through the incision into the artery and manipulated into position by threading it through a sequence of arteries, which may include branches, turns, and other obstructions.

Once the cardiac electrode catheter has been maneuvered into the region of interest, the electrodes at the distal end of the catheter are placed against the anatomical feature or area sought to be diagnosed or treated. This can be a difficult procedure. The electrophysiologist manipulating the catheter typically can only do so by operating a system of controls at the proximal end of the catheter shaft. The catheter can be advanced and withdrawn longitudinally by pushing and pulling on the catheter shaft, and can be rotated about its axis by rotating a control at the proximal end. Both of these operations are rendered even more difficult by the likelihood that the catheter must be threaded through an extremely tortuous path to reach the target area. Finally, once the tip of the catheter has reached the target area, the electrodes at the distal end of the catheter are placed in proximity to the anatomical feature, and diagnosis or treatment can begin.

In the past, the difficulties experienced by electrophysiologists in the use of a cardiac electrode catheter have been addressed in a number of different ways.

To facilitate maneuvering a catheter through a tight and sinuous sequence of arterial passageways, catheters having a pre-shaped curve at their distal end have been developed. To negotiate the twists and branches common in a patient's arterial system, the catheter typically is rotatable to orient the pre-shaped curve in a desired direction. Although the tip of the catheter may be somewhat flexible, the curve is fixed into the catheter at the time of manufacture. The radius and extent of the curvature generally cannot be altered. Therefore, extensive pre-surgical planning is frequently necessary to determine what curvature of catheter is necessary. If the predicted curvature turns out to be incorrect, the entire catheter may need to be removed and replaced with one having the proper curvature. This is an expensive and time-consuming ordeal, as catheters are generally designed to be used only once and discarded. Moreover, the additional delay may place the patient at some additional risk.

A variation of the pre-shaped catheter uses a deflectable curve structure in the tip. This type of catheter has a tip that is ordinarily substantially straight, but is deflectable to assume a curved configuration upon application of force to the tip. However, the tip deflection is not remotely controllable. In a certain patient's arterial system, a point may be reached at which the proper force cannot be applied to the catheter tip. In such cases, the catheter must be withdrawn and reinserted through a more appropriate passage, or another catheter with a different tip configuration must be used.

Another attempt to facilitate the placement of catheters takes the form of a unidirectional steering catheter. A typical unidirectional steering catheter has a steering mechanism, such as a wire, that extends the length of the catheter to the distal tip. The steering mechanism is coupled to the tip in such a way that manipulation of the proximal end of the mechanism (e.g., by pulling the steering wire) results in deflection of the catheter tip in a single direction. This type of catheter is illustrated, for example, in U.S. Pat. No. 5,125,896 issued to Hojeibane. The direction of deflection can be controlled by embedding a ribbon of wire in the tip; the ribbon is flexible along one dimension but not in others. This type of catheter can further be controlled by rotating the entire shaft of the catheter; in this manner, the direction of bend within the patient can be controlled. The shaft of such a catheter must be strong enough to transmit torque for the latter form of control to be possible.

Bidirectional steering catheters also exist. The distal end of a bidirectional steering catheter can be maneuvered in two planes, allowing the tip to be positioned with greater accuracy. However, bidirectional steering catheters are complex mechanically and are often difficult to manipulate.

Although the foregoing types of catheters address the issue of maneuverability in different ways, none of them is ideally configured to maintain contact with and apply a desired amount of pressure to a desired anatomical feature, such as an atrial wall.

One device used for the latter purpose is known as a basket catheter. See, for example, the HIGH DENSITY MAPPING BASKET CATHETER manufactured by Cardiac Pathways Corporation. A basket catheter has several spring-biased arms near the distal tip. When these arms are unconstrained, they bow outward to define a basket-like shape. The arms of the basket are constrained for implantation in a sheath structure. When the tip of the catheter has reached the desired location, the sheath is retracted, or the arms are advanced out of the sheath.

However, because the tip of the catheter is sheathed, it is not easily steerable into location, and is not as flexible as one might desire. Moreover, the sheath adds bulk to the device, which might significantly limit the range of applications in which the basket catheter can be used. The basket has only one shape and size. Once the arms are deployed from the sheath, the basket assumes a single configuration defined upon manufacture. If the predefined configuration of the basket is not suitable, then substantially no correction is possible. Also, known basket catheters are not indicated for use in high-energy therapeutic applications, such as ablation.

A variable-geometry sheathed electrode catheter is also known in the art. This device has a single electrode-bearing tip portion that is initially disposed within a relatively inflexible sheath. When the tip portion is advanced with respect to the sheath, the tip portion bows out of a slot-shaped aperture in the sheath. The shape of the tip portion can be controlled to apply a desired amount of pressure to an anatomical feature. However, as a sheath is used around the catheter, the device is not easily steerable into location. Moreover, as discussed above, the sheath structure adds undesirable bulk to the device.

Radio frequency ablation (RFA) has become the treatment of choice for specific rhythm disturbances. To eliminate the precise location in the heart from which an arrhythmia originates, high frequency radio waves are generated onto the target tissue, whereby heat induced in the tissue burns the tissue to eliminate the source of arrhythmia.

U.S. Pat. No. 5,617,854 to Munsif describes, inter alia, a pre-shaped catheter particularly useful for ablating in the vicinity of the sinoatrial node, the left atrium, and up to the mitral valve. The tip of the catheter is formed of a temperature-sensitive shape-memory material, e.g., Nitinol, or is otherwise invoked to assume a segmented configuration upon reaching a desired position. The segmented configuration includes proximal and distal segments which are generally parallel. The distal segment includes an ablation electrode. In operation, the segmented shape produces tension which urges the ablation electrode on the distal segment into contact with a wall of the left atrium, while the proximal segment is urged against other tissue. Since the shape of the catheter tip is fixed, the catheter tip is not easily manipulated. Further, the tension produced between the segments of the catheter tip is dependent on the shape and dimensions of the ablation site, e.g., the left atrium.

It is well known that aberrant heart activity such as arrhythmia may result from signals originating at the pulmonary veins. Unfortunately, it is particularly difficult to perform electrophysiological investigation and treatment at the pulmonary veins using existing ablation catheters.

Guiding and maneuvering a catheter towards and within the pulmonary veins is difficult due to the location, dimensions and structure of the pulmonary veins. Specifically, the average diameter of the pulmonary veins is on the order of 25 mm, i.e., at least one order of magnitude larger than the diameter of a typical catheter shaft which is adapted to be guided in relatively narrow arteries. This difference in dimensions makes it difficult to maintain continuous, controlled, contact between the catheter tip and the wall of the pulmonary vein. Further, it is difficult to manipulate the catheter tip from the relatively large space of the left atrium into a given pulmonary vein and to insert the catheter tip into the pulmonary vein. This limited maneuverability of the catheter towards and within the pulmonary veins is time consuming and results in inaccurate positioning of mapping and/or ablation electrodes along the inner walls of the pulmonary veins.

Further, the pulmonary veins have a rubbery tissue which is particularly susceptible to perforation and must, thus, be treated with extreme care to avoid damage. Unfortunately, the more maneuverable catheters described above, e.g., the "basket" type catheter and the variable-geometry, sheathed catheter, which theoretically could be used to engage the inner wall of the pulmonary veins, have complex structures which are most likely to damage the tissue of the pulmonary veins. Therefore, existing catheters cannot be used to safely and effectively investigate and/or ablate tissue along the inner walls of the pulmonary veins.

Accordingly, there is a need for a cardiac electrode catheter that can be conveniently steered into a relatively wide blood vessel, e.g., a pulmonary vein, and that can be controlled to efficiently and continuously engage desired sites on the inner wall of the blood vessel without causing damage to the blood vessel.

SUMMARY OF THE INVENTION

The present invention seeks to provide a steerable electrode catheter which can be conveniently guided to a target blood vessel, e.g., a pulmonary vein, and that can be inserted into the target blood vessel in a physical configuration which allows continuous, efficient and safe engagement between at least one electrode on the catheter and the inner surface of the blood vessel.

The electrode catheter of the present invention and the method of its use are adapted to address the problems associated with mapping and/or ablating tissue on the inner walls of a relatively wide blood vessel, particularly a pulmonary vein.

The electrode catheter of the present invention has a relatively flexible distal end portion adapted to be deflected from a generally straight configuration into a J-shaped configuration before insertion into a target blood vessel, e.g., one of the pulmonary veins.

The J-shaped configuration includes a generally straight proximal section, a curved middle section and a generally straight distal section. The proximal section includes at least one ablation electrode, hereinafter referred to as the proximal ablation electrode, and at least one mapping electrode, hereinafter referred to as the proximal mapping electrode. Similarly, the distal section includes at least one ablation electrode, hereinafter referred to as the distal ablation electrode, and at least one mapping electrode, hereinafter referred to as the distal mapping electrode.

In the J-shaped configuration, the proximal and distal sections simultaneously engage two diametrically opposite regions on the inner wall of the target blood vessel. Thus, the proximal and distal mapping electrodes engage substantially diametrically opposite sites on the inner surface of the blood vessel. In a preferred embodiment of the invention, the proximal and distal ablation electrodes engage sites contiguous to the sites engaged by the proximal and distal mapping electrodes, respectively. This enables a surgeon to continuously map the electrical activity along the inner wall of the blood vessel and to selectively ablate tissue at suspect sources of aberrant heart activity.

The steering mechanism of the electrode catheter of the present invention is used both to maneuver the tip of the catheter, e.g., within the left atrium, to a suitable position vis-a-vis a target blood vessel, e.g., one of the pulmonary veins, and to subsequently deflect the catheter tip into the J-shaped configuration before insertion of the catheter into the target blood vessel.

Any steering mechanism known in the art may be used for deflecting the catheter tip into desired configurations. For example, the steering mechanism may include a control wire which extends the length of the catheter and is attached to the distal end of the catheter tip.

When the distal end portion engages the inner wall of the target blood vessel, the proximal and distal mapping electrodes provide outputs responsive to the electric potential at the diametrically opposite sites engaged by the two electrodes. Based on these outputs, a surgeon can determine the location of possible sites on the inner wall of the pulmonary vein where aberrant heart activity may originate. The surgeon may then ablate these sites by activating the proximal and/or distal ablation electrodes to ablate one or two, substantially diametrically opposite, sites on the inner wall of the pulmonary vein.

It has been found by the present inventors that once a source of arrhythmia has been detected at a certain position along the longitudinal axis of the pulmonary vein, an effective treatment of that source includes ablation of a plurality of circumferentially spaced sites at the longitudinal position of the detected source. Therefore, the present invention provides a method of treating arrhythmia originating from a blood vessel, e.g., a pulmonary vein, including the steps of detecting a source of arrhythmia along the longitudinal axis of the blood vessel and ablating a plurality of circumferentially spaced sites on the inner wall of the blood vessel substantially at the longitudinal position where the source of Arrhythmia is detected.

In an embodiment of the present invention, after one or two sites are ablated by the proximal and/or distal ablation electrodes, the distal end portion of the catheter is rotated about the longitudinal axis of the catheter to cause a circumferential displacement of the proximal and distal ablation electrodes along the inner wall of the pulmonary vein. In this embodiment, the electrode catheter may be used to ablate any number of circumferentially spaced sites on the inner wall of the pulmonary vein, by ablating one or two sites at each circumferential position. Typically, 2–6 circumferentially spaced sites are ablated at each longitudinal position of the blood vessel at which a source of arrhythmia is detected. The spacing between the ablated sites is controlled by the amount of rotation of the catheter between ablation sessions.

Any rotation mechanism can be used to control the rotation of the catheter tip about the longitudinal axis of the catheter. For example, the catheter may be formed of a rotationally stiff material, whereby rotation of the proximal end of the catheter causes corresponding rotation of the catheter tip. Alternatively, the catheter may include a hollow tube and the rotation mechanism may include a longitudinal rotationally stiff member extending through the hollow tube.

The proximal and distal ablation electrodes and the proximal and distal mapping electrodes are preferably all ring electrodes. This enables all four electrodes to engage the inner wall of the target blood vessel when the catheter is inserted in its J-shaped configuration, regardless of the plane in which the distal end portion is deflected into the J-shaped configuration.

In a preferred embodiment of the invention, the proximal and distal ablation electrodes are associated with proximal and distal temperature sensors, e.g., thermocouples, which provide outputs responsive to the temperature in a vicinity of the proximal and distal ablation electrodes, respectively. The temperature sensors are preferably embedded in the catheter and are thermally associated with the respective ablation electrodes.

BRIEF DESCRIPTION OF THE DRAWINGS

The present invention will be understood and appreciated more fully from the following detailed description of the preferred embodiment taken in conjunction with the accompanying drawings in which:

FIG. 1A is a perspective view, schematic, illustration of an ablation catheter in accordance with an embodiment of the present invention;

DETAILED DESCRIPTION OF A PREFERRED EMBODIMENT

Figure 4:
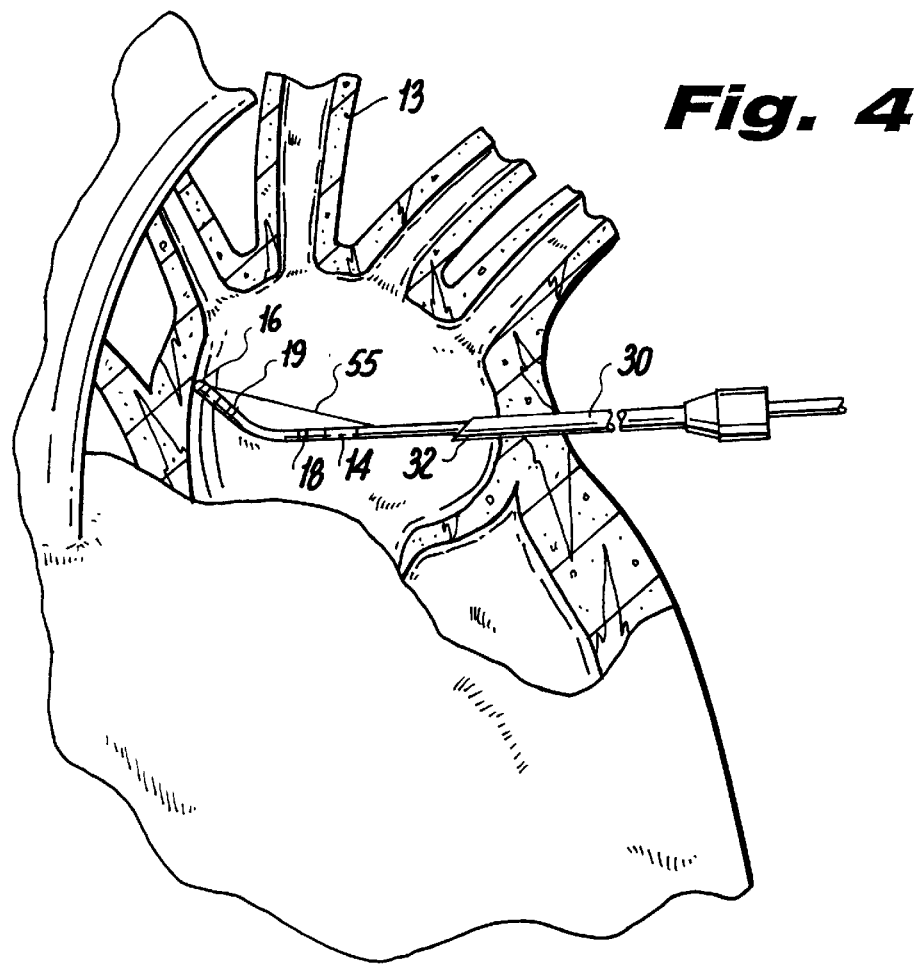
FIG. 4 is a longitudinal sectional view of a distal tip portion of the catheter of FIG. 1A in a partly deflected configuration during manipulation of the catheter towards one the pulmonary veins.

Reference is made to FIG. 1A which schematically illustrates a perspective view of an ablation catheter 10 in accordance with an embodiment of the present invention.

Catheter 10 includes a handle portion 22, electric connectors 24, a tubular catheter shaft 11 and a tip portion 12. According to the present invention, tip portion 12 is deflectable from a generally straight configuration, indicated by the solid lines in FIG. 1, to a J-shaped configuration, indicated by the broken lines in FIG. 1A. Tip portion 12 accommodates a proximal ablation electrode 14, a proximal mapping electrode 18, a distal ablation electrode 16 and a distal mapping electrode 19.

Figure 1B:
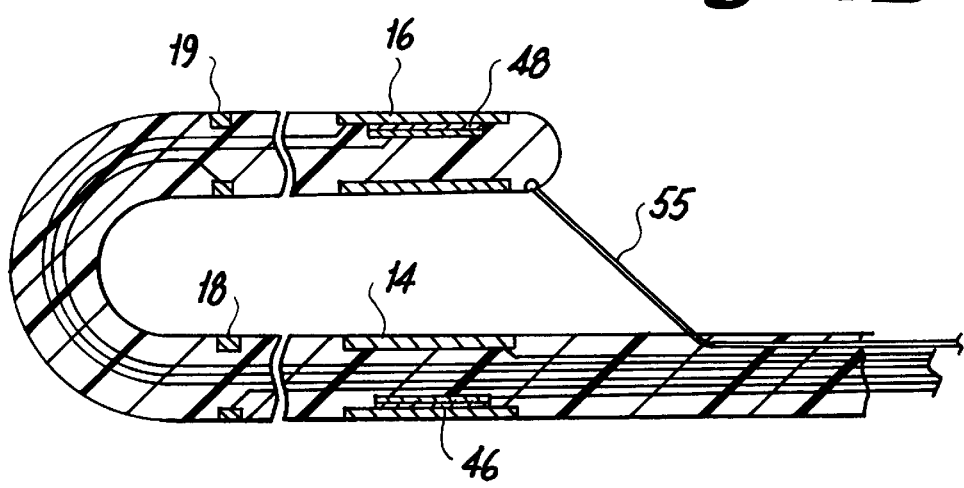
FIG. 1B is a schematic, cross sectional, illustration of a distal tip portion of the ablation catheter of FIG. 1A.

Reference is also made to FIG. 1B which schematically illustrates a cross-section of tip portion 12 in its the J-shaped configuration. As shown in FIG. 1B, electrodes 14, 16, 18 and 19, are preferably ring-electrodes covering the circumference of catheter 10. In a preferred embodiment of the present invention, catheter 10 further includes temperature sensors 46 and 48, which are thermally associated with ablation electrodes 14 and 16, respectively.

In its J-shaped configuration, tip portion 12 has a proximal section 40, accommodating electrodes 14 and 18, a distal section 42, accommodating electrodes 16 and 19, and an intermediate curved section 43. Proximal section 40 and distal section 42 are generally parallel with a predetermined separation therebetween. Curved section 43 is preferably more flexible than the sections 40 and 42. Thus, when tip portion 12 is deflected, as described in detail below, only section 43 is curved while sections 40 and 42 remain substantially straight.

Sensors 46 and 48 may include thermocouples or any other temperature sensors know in the art that provide outputs corresponding to the temperature of electrodes 14 and 16, respectively. When electrodes 14 and/or 16 are activated to ablate target tissues, as described in detail below, the outputs of sensors 46 and 48 are indicative of the temperatures of the ablated tissues.

Handle portion 22 includes deflection controls 26, for controlling the deflection of catheter tip 12, and ablation controls 27 which control the activation of ablation electrodes 14 and 16, as described below. Handle portion 22 is preferably also used for rotation of tip portion 12. In an embodiment of the present invention, catheter shaft 11 is formed of a rotationally inflexible material, as is known in the art, whereby rotation of handle portion 22 about the longitudinal axis of catheter 10 causes corresponding rotation of tip portion 12.

Catheter 10 includes a deflection mechanism for deflecting tip portion 12 into a J-shaped configuration or any other configuration, as described in detail below. The deflection mechanism may include any suitable mechanism known in the art, for example, a control wire 55 which extends along catheter shaft 11 from handle portion 22 to the distal end of tip portion 12. If such a mechanism is used, a proximal portion of control wire 55 may be disposed within the interior of catheter shaft 11. As control wire 55 approaches the relatively flexible tip portion 12, it may exit shaft 11 through an aperture and extend along the exterior of the catheter tip. The distal end of control wire 55 is coupled to the distal end of tip portion 12.

In an alternative embodiment of the present invention, catheter 10 includes a bi-directional deflection mechanism, whereby the catheter can be simultaneously deflected in two different planes. This allows more efficient maneuvering of tip portion 12 towards a target blood vessel and enables deflection of the tip portion into the J-shaped or any other desired configuration before insertion of tip portion 12 into the target blood vessel. The bidirectional steering mechanism may include first and second control wires similar to control wire 55 described above, whereby each wire controls the steering of tip portion 12 in a different plane. The deflection of catheter tip 12 into a desired configuration is preferably controlled by the surgeon using controls 26 on handle portion 22, as is known in the art.

In an embodiment of the present invention, the surgeon may rotate tip portion 12 about the longitudinal axis of catheter 10. Any rotation mechanism can be used to control the rotation of the catheter tip. For example, catheter shaft 11 may transmit the rotation from handle portion 22 to catheter tip 12, as described above. Alternatively, the rotation mechanism of catheter 10 may include a rotationally stiff member extending longitudinally through the interior of catheter shaft 11.

In a preferred embodiment of the present invention, electrodes 14, 16, 18 and 19 and sensors 46 and 48 are separately addressable via six of connectors 24, namely connectors, 34, 36, 38, 39, 56 and 58, respectively. Connectors 34, 36, 38, 39, 56 and 58 are connected to their respective electrodes and sensors by conductors 52 which preferably extend along the interior of catheter shaft 11.

Using connectors 38 and 39, electrodes 18 and 19 are connected to mapping circuitry which monitors the electrical activities, e.g., the electric potentials, of tissue in contact with electrodes 18 and 19, respectively. In a preferred embodiment of the invention, an output of the mapping circuitry is visually displayed to the surgeon, as is known in the art, to provide the surgeon with on-line mapping of the tissue.

Using connectors 34 and 36, electrodes 14 and 16 are connected to respective ablation energizing circuits, which are preferably separately controlled by respective ablation controls 27. Upon activation, the energizing circuits energize electrodes 14 and/or 16 with radio frequency (RF) energy, as is known in the art. Using separate controls 27, the surgeon may selectively activate either or both of electrodes 14 and 16 to selectively ablate tissue, as described in detail below.

Using connectors 46 and 48, temperature sensors 46 and 48 are connected to temperature monitoring circuitry which monitors the temperatures of tissues in contact with electrodes 14 and 16, respectively. In a preferred embodiment of the invention, an output of the temperature monitoring circuitry is visually displayed to the surgeon, as is known in the art, to provide the surgeon with on-line indication of the tissue temperatures.

According to the present invention, catheter 10 is used for mapping and/or ablating tissue on the inner walls of a blood vessel, e.g. a pulmonary vein, of a patient suffering from aberrant heart activity, e.g., Cardiac Arrhythmia. In an embodiment of the present invention, pulmonary veins selected for examination and/or treatment are accessed from the left atrium, preferably using an introduction and guidance procedure as described below with reference to FIGS. 2–5.

FIGS. 2–5 schematically illustrate a procedure for introducing catheter 10 into the left atrium and subsequently guiding tip portion 12 of catheter 10 into one of the pulmonary veins.

Figure 2:
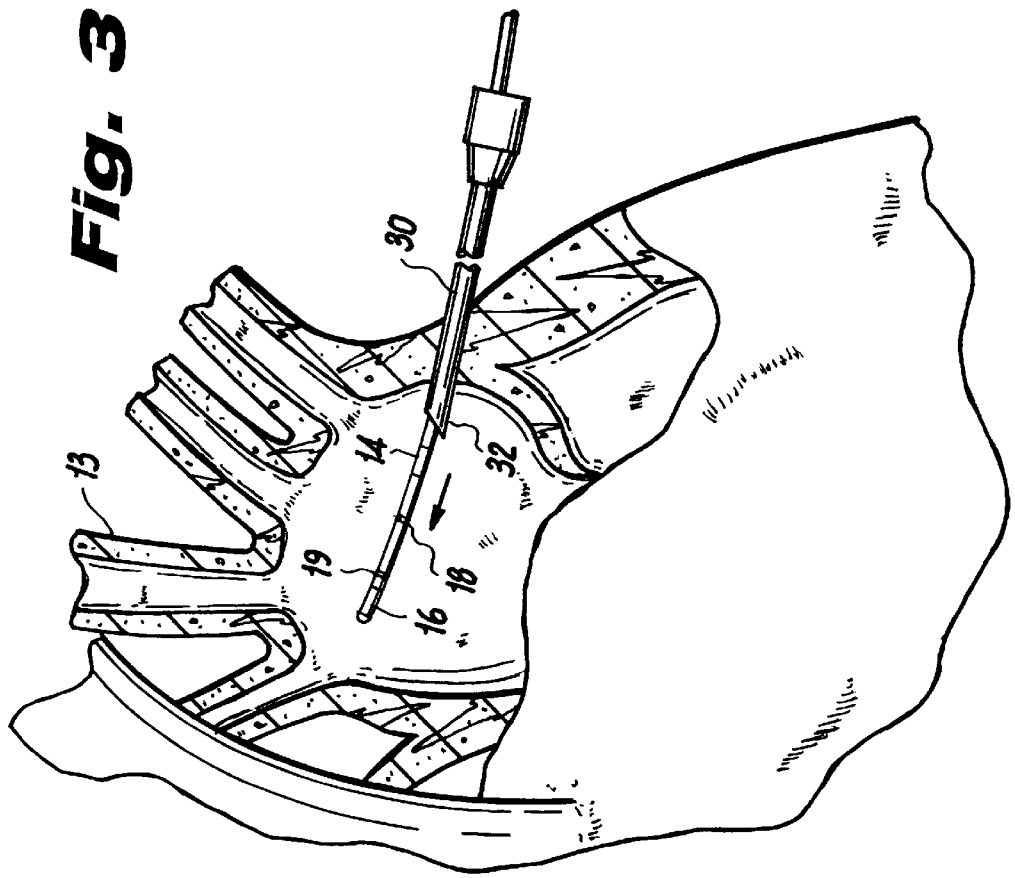
FIG. 2 is a cross sectional illustration of the left atrium of a patient showing an introducer sheath in the atrium wall for introducing the catheter of FIG. 1A into the atrium chamber.

As shown in FIG. 2, an introducer sheath 30 having a sharp edged, preferably slanted, tip 32 is used to puncture the left atrium of the heart. The sharp tip 32 of sheath 30 ensures "clean" puncturing of the atrial wall with minimum damage to the wall tissue. Sheath 30 has a hollow interior which defines a channel for introducing catheter 10 into the left atrium. The inner diameter of sheath 30 is preferably equal to or slightly larger than the diameter of catheter shaft 11, to prevent undesired leakage between the catheter shaft and the sheath.

Figure 3:
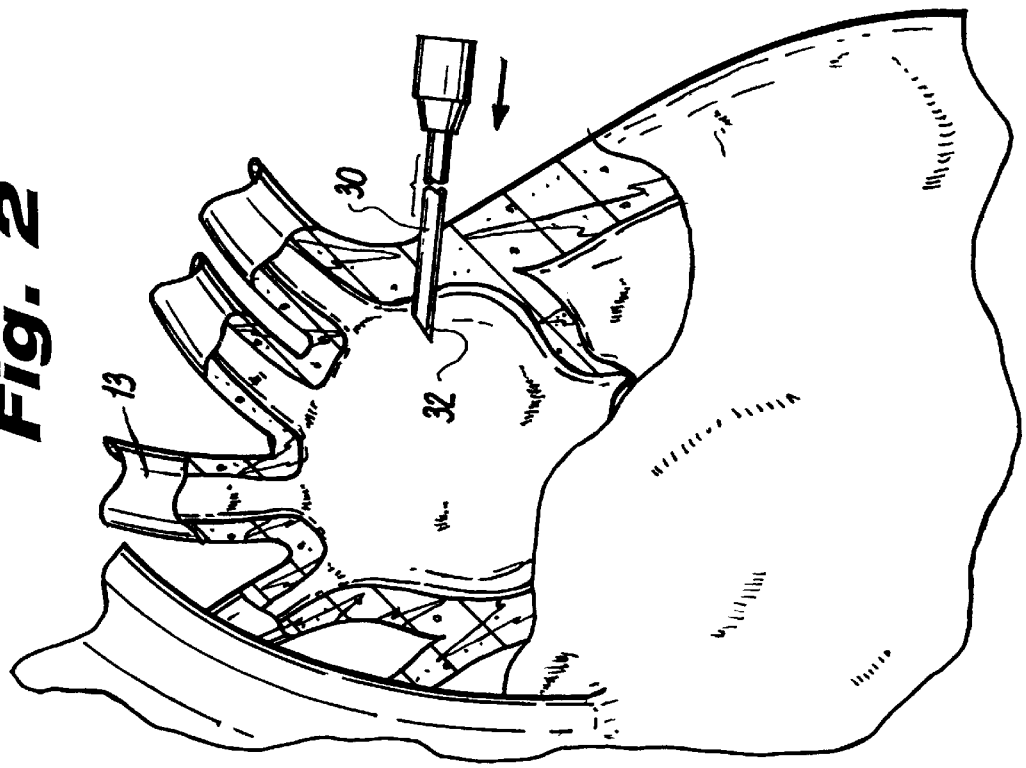
FIG. 3 is a longitudinal sectional view of the distal tip portion of the catheter of FIG. 1A in a generally straight configuration showing the catheter being is introduced into the left atrium via the introducer sheath of FIG. 2.

FIG. 3 schematically illustrates tip portion 12 of catheter 10 being introduced into the left atrium via introducer sheath 30.

Figure 5:
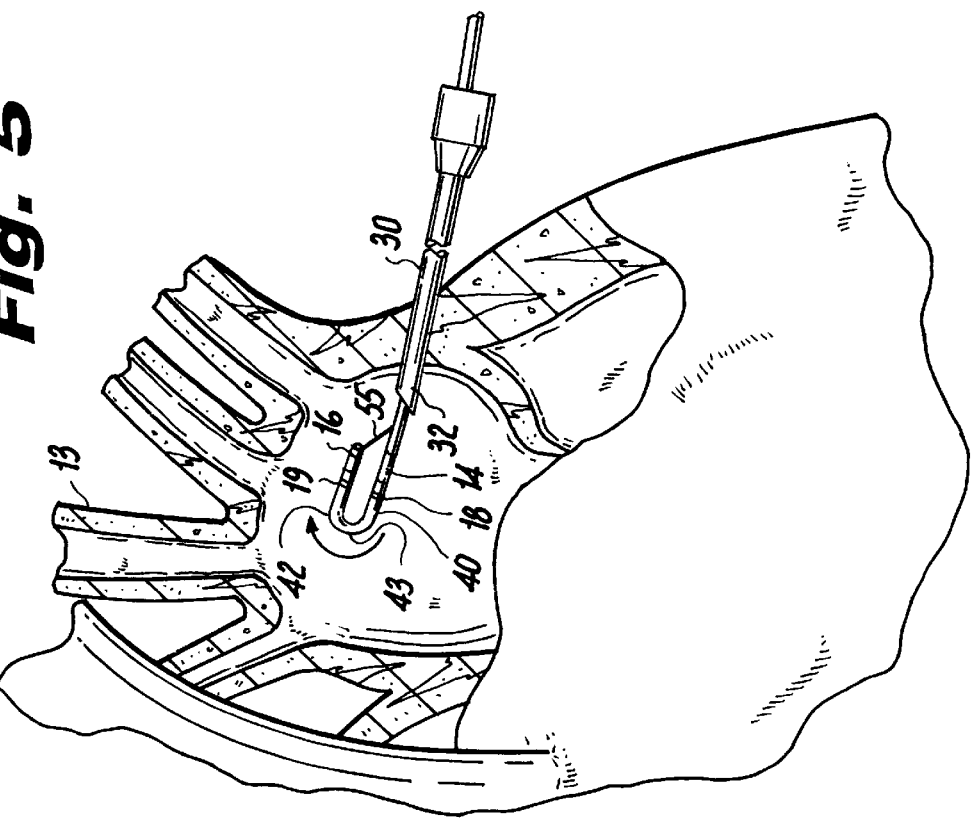
FIG. 5 is a longitudinal sectional view of the distal tip portion of the catheter of FIG. 1A in a fully deflected configuration in preparation for insertion of the catheter into one of the pulmonary veins of the patient.

Reference is now made to FIGS. 4 and 5. Once tip 12 of catheter 10 is introduced into the left atrium, the surgeon proceeds to guide tip portion 12 towards one of the pulmonary veins, e.g., a pulmonary vein 13. The steering/deflection mechanism of catheter 10 may be utilized to manipulate tip portion 12 against the inner walls of the left atrium, thereby to expedite the guiding of tip portion 12 towards pulmonary vein 13. For example, tip portion 12 may be guided by "stepping" the catheter tip along the inner wall of the left atrium, e.g., by alternately engaging and disengaging the atrial wall and varying the curvature of tip portion 12, until reaching pulmonary vein 13. Additionally, if necessary, shaft 11 may be rotated to assist in the manipulation of tip portion 12.

By virtue of the continuous steering capability of catheter 10, a surgeon can produce any desired configuration of tip portion 12 as the catheter tip is guided and manipulated towards pulmonary vein 13. For example, tip potion 12 can be guided in a generally straight configuration, as shown in FIG. 3, a partly deflected configuration, as shown in FIG. 4, or a fully deflected configuration, as shown in FIG. 5, depending on the manipulation requirements encountered by the surgeon.

Once tip portion 12 is brought into a desired position vis-a-vis pulmonary vein 13, catheter tip 12 is deflected in the direction indicated by arrow 45 into the J-shaped configuration shown in FIG. 5. In the J-shaped configuration, as described above, tip portion 12 includes proximal section 40, distal section 42 and intermediate curved section 43, wherein proximal section 40 and distal section 42 are generally parallel with a predetermined separation therebetween. In a preferred embodiment of the invention, the separation between sections 40 and 42 corresponds to the inner diameter, d, of the blood vessel being treated, e.g., pulmonary vein 13. It should be appreciated, however, that the continuous steering mechanism of catheter 10 enables the surgeon to control the separation between section 40 and 42, to a certain extent, e.g., by controlling the curvature of curved section 43.

Figure 6:
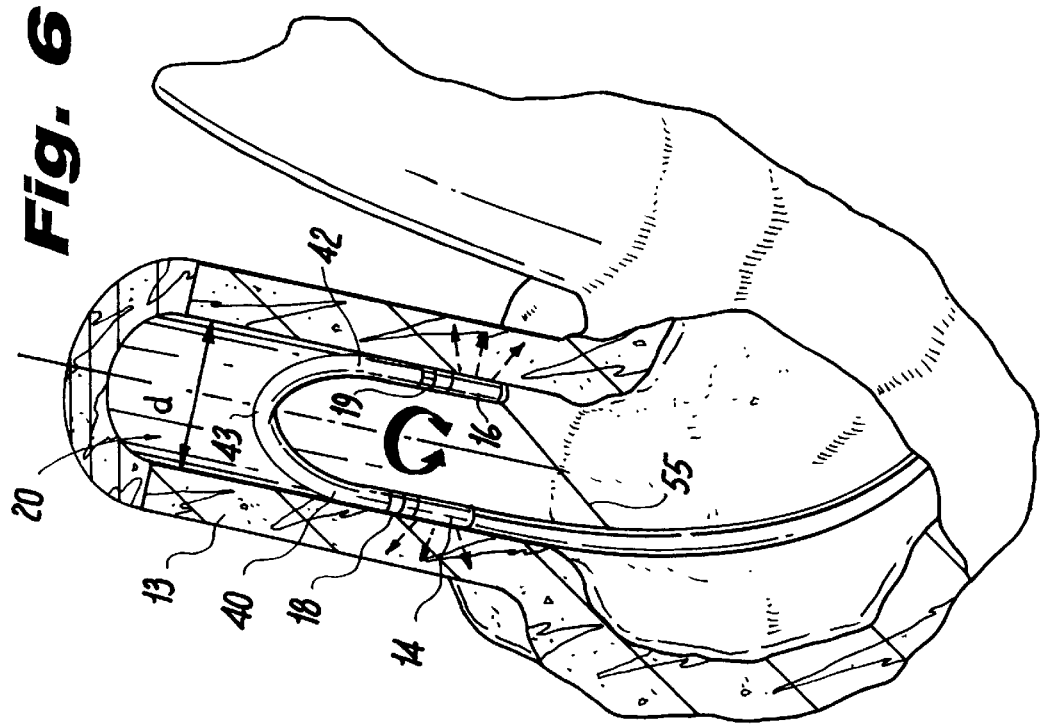
FIG. 6 is a longitudinal sectional view of the distal tip portion of the catheter of FIG. 1A in a fully deflected configuration within the pulmonary vein of the patient.

Reference is now made to FIG. 6 which schematically illustrates tip portion 12 of catheter 10 engaging the inner wall surface 20 of pulmonary vein 13. As mentioned above, the separation between section 40 and 42 corresponds to the inside diameter, d, of the blood vessel being treated, e.g., pulmonary vein 13. In a preferred embodiment of the invention, catheter 10 remains in its deflected, J-shaped, configuration for the entire period during which the tip portion engages wall surface 20 of blood vessel 13.

In the J-shaped configuration, proximal section 40 and distal section 42 are in contact with diametrically opposite regions on wall surface 20 of blood vessel 13. Thus, mapping electrodes 18 and 19 engage diametrically opposite sites of inner wall surface 20. By virtue of the mapping circuitry described above, electrodes 18 and 19 provide outputs responsive to the electric potential at the diametrically opposite sites engaged thereby, which outputs are preferably visually displayed to the surgeon. Based on the outputs from mapping electrodes 18 and 19, the surgeon locates sites on wall surface 20 requiring ablation treatment, e.g., sources of Cardiac Arrhythmia, as is known in the art.

In the J-shaped configuration, ablation electrodes 14 and 16 are generally parallel and engage diametrically opposite sites contiguous with the sites engaged by mapping electrodes 18 and 19, respectively. Depending on the reading from electrodes 18 and 19, either or both of electrodes 14 and 16 may be activated to ablate one or two sites, respectively, on wall surface 20 of pulmonary vein 13. After each such ablation session, tip portion 12 may be rotated, using the rotation mechanism described above, about an axis 50 generally parallel to catheter shaft 11. After such rotation, either or both of ablation electrode 14 and 16 may be re-activated to ablate one or two additional sites along the circumference of wall surface 20. This procedure may be repeated a number of times until a desired number of sites are ablated along the circumference of wall surface 20. The total number of ablations required for each longitudinal position at which a source of aberrant heart activity is detected varies from patient to patient. Typically, 2–6 sites circumferentially spaced sites are ablated at each longitudinal position of aberrant heart activity detected along the pulmonary veins.

As described above, electrodes 14 and 16 are preferably associated with temperature sensors 46 and 48, respectively, which may include thermocouples or any other temperature sensing devices known in the art. Based on the outputs of temperatures sensors 46 and 48, the temperature monitoring circuitry provides the surgeon with a reading of the temperatures of electrodes 14 and 16, respectively. These temperatures correspond to the temperatures of the diametrically opposite sites being ablated on inner wall surface 20. Thus, the surgeon can deactivate either or both of electrodes 14 and 16 when the temperature of the ablated sites exceeds a predetermined threshold. Once the temperature of the ablated sites drops below the predetermined threshold, the surgeon may reactivate electrodes 14 and/or 16 if further ablation is required at the same sites.

It should be appreciated that the present invention is not limited to the specific embodiments described hereinabove with reference to the accompanying drawing. Rather, the scope of the present invention is limited only by the following claims:

We claim:

1. A catheter for ablating and/or mapping tissue on the inner wall of a blood vessel comprising:

a body portion; and a tip portion having a proximal section and a distal section, the proximal section including a proximal ablation electrode and a proximal mapping electrode and the distal section including a distal ablation electrode and a distal mapping electrode, wherein said tip portion is deflectable from a first, generally straight, configuration in which the proximal and distal sections are substantially co-linear to a second, J-shaped, configuration in which the proximal and distal sections are generally parallel with a separation therebetween substantially corresponding to the inside diameter of said blood vessel.

2. A catheter according to claim 1 wherein said blood vessel is a pulmonary vein.

3. A catheter according to claim 1 and further comprising a proximal temperature sensor thermally associated with the proximal ablation electrode and a distal temperature sensors thermally associated with the distal ablation electrode.

4. A catheter according to claim 3 wherein said blood vessel is a pulmonary vein.

5. A method for ablating tissue on the inner wall of a blood vessel comprising the steps of:

inserting into said blood vessel a catheter tip portion having a proximal section and a distal section, the proximal section including a proximal ablation electrode and a proximal mapping electrode and the distal section including a distal ablation electrode and a distal mapping electrode, said tip portion having a J-shaped configuration in which the proximal and distal sections are generally parallel and engage first and second, diametrically opposite, regions of said inner wall of the blood vessel;

monitoring the output of at least one of the proximal and distal mapping electrodes to detect a source of aberrant heart activity on said inner wall; and selectively activating at least one of the proximal and distal ablation electrodes to ablate tissue in at least one of said first and second regions.

6. A method according to claim 5 wherein said blood vessel is a pulmonary vein.

7. A method according to claim 5 and further comprising, after the step of activating at least one of said proximal and distal electrodes to ablate tissue in at least one said first and second regions, a step of rotating said catheter tip about a longitudinal axis such that said proximal and distal sections engage third and fourth, diametrically opposite, regions of said inner wall, and subsequently ablating tissue in at least one of said third and fourth regions.

8. A method according to claim 7 wherein said blood vessel is a pulmonary vein.

\* \* \* \* \*